United States Patent
Fujita et al.

(10) Patent No.: US 9,612,215 B2
(45) Date of Patent: Apr. 4, 2017

(54) SUSCEPTOR

(75) Inventors: Ichiro Fujita, Kagawa (JP); Hirokazu Fujiwara, Kagawa (JP)

(73) Assignee: TOYO TANSO CO., LTD., Osaka-shi (JP)

( * ) Notice: Subject to any disclaimer, the term of this patent is extended or adjusted under 35 U.S.C. 154(b) by 1041 days.

(21) Appl. No.: 11/632,999

(22) PCT Filed: Jul. 1, 2005

(86) PCT No.: PCT/JP2005/012215
§ 371 (c)(1),
(2), (4) Date: Feb. 13, 2007

(87) PCT Pub. No.: WO2006/008941
PCT Pub. Date: Jan. 26, 2006

(65) Prior Publication Data
US 2008/0035632 A1 Feb. 14, 2008

(30) Foreign Application Priority Data
Jul. 22, 2004 (JP) ................. 2004-213845

(51) Int. Cl.
*G01N 23/225* (2006.01)
*C23C 16/458* (2006.01)
(Continued)

(52) U.S. Cl.
CPC ..... *G01N 23/2258* (2013.01); *C23C 16/4581* (2013.01); *C30B 25/12* (2013.01); *C30B 29/36* (2013.01); *H01L 21/68757* (2013.01)

(58) Field of Classification Search
CPC G01N 23/2258; C23C 16/4581; C30B 25/12; C30B 29/36; H01L 21/68757
(Continued)

(56) References Cited

U.S. PATENT DOCUMENTS 4,123,571 A  10/1978  Balog et al.
5,194,408 A *  3/1993  Stamp et al. .................. 501/88
(Continued)

FOREIGN PATENT DOCUMENTS

DE  198 03 423  8/1999
EP  1 528 121  5/2005
(Continued)

OTHER PUBLICATIONS

Office Action issued Nov. 21, 2008 in P.R. China application No. 200580024815.2.*
(Continued)

*Primary Examiner* — Jeffrie R Lund
(74) *Attorney, Agent, or Firm* — Oblon, McClelland, Maier & Neustadt, L.L.P.

(57) ABSTRACT

The invention provides a susceptor capable of obtaining high-quality SiC semiconductor crystals by keeping the Si concentration and C concentration around a wafer constant and by preventing the generation of particles. A susceptor of graphite covered with silicon carbide is characterized in that at least one section of a part on which a wafer is placed is tantalum carbide or a graphite material covered with tantalum carbide. The part on which the wafer is placed may be a detachable member. A material around the part on which the wafer is placed may be a detachable graphite material covered with silicon carbide.

12 Claims, 6 Drawing Sheets

(51) Int. Cl.
  *C30B 25/12* (2006.01)
  *C30B 29/36* (2006.01)
  *H01L 21/687* (2006.01)

(58) Field of Classification Search
  USPC .................................................. 118/715, 728
  See application file for complete search history.

(56) References Cited

U.S. PATENT DOCUMENTS

| | | | | |
|---|---|---|---|---|
| 5,256,887 | A * | 10/1993 | Yang | 257/53 |
| 5,558,721 | A * | 9/1996 | Kohmura | F01D 15/067 |
| | | | | 118/500 |
| 5,584,936 | A * | 12/1996 | Pickering | C23C 16/4583 |
| | | | | 118/500 |
| 5,820,686 | A * | 10/1998 | Moore | C23C 16/4581 |
| | | | | 118/500 |
| 6,007,635 | A * | 12/1999 | Mahawili | C23C 16/4584 |
| | | | | 118/500 |
| 6,090,212 | A * | 7/2000 | Mahawili | C23C 16/4584 |
| | | | | 118/500 |
| 6,129,047 | A * | 10/2000 | Nakamura | C23C 16/4412 |
| | | | | 118/500 |
| 6,325,858 | B1 * | 12/2001 | Wengert | C23C 16/4401 |
| | | | | 118/715 |
| 6,425,994 | B1 * | 7/2002 | Choi | H01L 21/67103 |
| | | | | 118/500 |
| 6,530,994 | B1 * | 3/2003 | Mahawili | 118/725 |
| 6,740,167 | B1 | 5/2004 | Rupp et al. | |
| 7,033,126 | B2 * | 4/2006 | Van Den Berg | 414/416.03 |
| 2003/0188687 | A1 * | 10/2003 | Paisley et al. | 118/730 |
| 2003/0221624 | A1 | 12/2003 | Jurgensen et al. | |
| 2003/0232001 | A1 * | 12/2003 | Fujita | 423/445 R |
| 2005/0062465 | A1 * | 3/2005 | De Ridder | 324/158.1 |
| 2005/0223994 | A1 * | 10/2005 | Blomiley | C23C 14/505 |
| | | | | 118/725 |
| 2012/0148744 | A1 * | 6/2012 | Colvin | C23C 16/46 |
| | | | | 427/255.11 |
| 2012/0149210 | A1 * | 6/2012 | Colvin | H05B 3/12 |
| | | | | 438/758 |

FOREIGN PATENT DOCUMENTS

| | | | |
|---|---|---|---|
| JP | 10-245285 | * | 9/1998 |
| JP | 2003-086518 | | 3/2003 |
| JP | 2003-86518 | | 3/2003 |
| JP | 2004-084057 | * | 3/2004 |
| JP | 2004-84057 | | 3/2004 |
| JP | 2004-507619 | | 3/2004 |
| JP | 2004-128271 | * | 4/2004 |
| WO | 99-43874 | | 9/1999 |
| WO | 03-039195 | | 5/2003 |
| WO | WO 03/088325 | * | 10/2003 |
| WO | WO 03/088325 A1 | | 10/2003 |
| WO | 2004-053188 | | 6/2004 |

OTHER PUBLICATIONS

Office Action issued Dec. 19, 2011, in Taiwan Patent Application No. 094123954 (with English language translation).

Office Action issued Mar. 19, 2012, in EPO Patent application No. 05 765 225.7-1215.

* cited by examiner

FIG.7A
FIG.7B
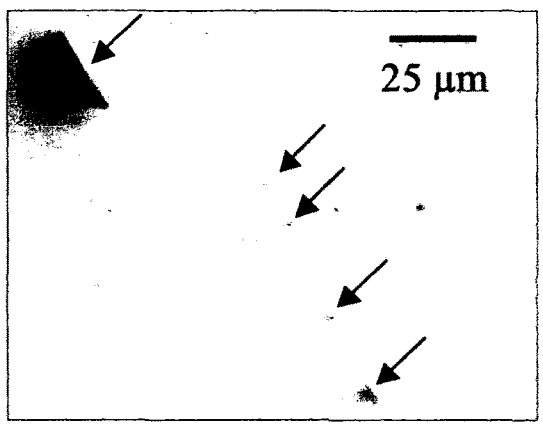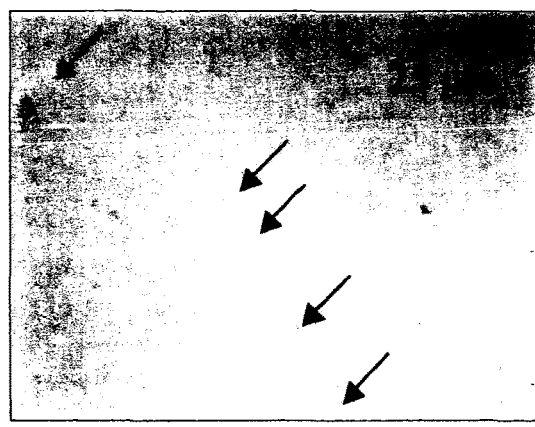

SUSCEPTOR

TECHNICAL FIELD

The present invention relates to a susceptor that is used for epitaxial growth and for thermal treatment, that is used in a semiconductor manufacturing process, and that is made of graphite covered with silicon carbide (hereinafter, referred to as "SiC").

BACKGROUND ART

Conventionally, a susceptor used to manufacture SiC semiconductors is well known. For example, a susceptor disclosed by Patent Document 1 mentioned below is known. The susceptor disclosed by this document is a carbon composite material composed of a carbon base material and a coating film made of tantalum carbide (hereinafter, referred to as "TaC") formed on the surface of the carbon base material. According to an analysis made by subjecting crystals forming the TaC-made film to X-ray diffraction, the carbon composite material is characterized in that the peak intensity ratio (i.e., I(200)/I(111)) of a peak corresponding to a (200) plane to a peak corresponding to a (111) plane is 0.2 to 0.5, or the peak intensity ratio (i.e., I(111)/I(200)) of a peak corresponding to a (111) plane to a peak corresponding to a (200) plane is 0.2 to 0.5.
Patent Document 1: Japanese Published Unexamined Patent Application No. 2004-84057

DISCLOSURE OF INVENTION

Problems to be Solved by the Invention

Generally, SiC epitaxial growth is performed at 1500° C. or more. If a SiC-covered graphite material is used as a susceptor in this temperature range, a SiC film that is a constituent of the susceptor is sublimated and abraded. Disadvantageously, this causes a fear that the SiC film that has been sublimated and evaporated will adhere to the reverse side of a wafer, and, as a result, the wafer and the susceptor cling to each other. Additionally, when a SiC layer is deposited on a TaC film during epitaxial growth on the condition that a TaC-covered graphite material is used as a susceptor, the SiC layer deposited thereon will be easily peeled off resulting from a difference in thermal expansion between the SiC layer and the TaC film. This occasionally causes the generation of particles.

In epitaxial growth and thermal treatment, to obtain a high-quality SiC semiconductor crystal, Si concentration and C concentration in an atmosphere around a wafer are required to be always kept constant during SiC epitaxial growth. However, in Patent Document 1, for example, the Si concentration and the C concentration in the atmosphere vary correspondingly to the progress of epitaxial growth. Therefore, in accordance with this, cases often occur in which atmosphere gas concentration that includes Si and C around the wafer varies greatly.

It is therefore an object of the present invention to provide a susceptor capable of obtaining a high-quality SiC semiconductor crystal by keeping the Si concentration and C concentration around a wafer constant and preventing the generation of particles without allowing the wafer and the susceptor to adhere to each other even after epitaxial growth is performed.

Means for Solving the Problems and Effects

The present invention is a susceptor of graphite covered with SiC, and is characterized in that at least one section of a part on which a wafer is placed is TaC or a graphite material covered with TaC. Preferably, when graphite is covered with a TaC film, the thickness of the TaC film is 10 to 100 µm. The reason why its thickness is 10 µm or more is that 10 µm is a minimum required thickness to completely cover the surface of the graphite base material therewith. More preferably, the thickness is 30 µm or more. The reason why its thickness is below 100 µm is from the viewpoint of time consumed for a covering operation, manufacturing costs, or dimensional accuracy of a product. Preferably, the part on which the wafer is placed is a detachable member. Preferably, a material around the part on which the wafer is placed is a detachable graphite material covered with silicon carbide.

According to the thus structured susceptor of the present invention, it is possible to obtain high-quality SiC semiconductor crystals by keeping the Si concentration and C concentration around the wafer constant and by preventing the generation of particles. Additionally, since the part on which the wafer is placed can be detached or since the part on which the wafer is placed and the area around this part can be detached, these can be easily exchanged for another, for example, even when these deteriorate after epitaxial growth or thermal treatment is performed a plurality of times. As a result, members made of graphite covered with SiC excluding the part on which the wafer is placed or excluding the part on which the wafer is placed and the area around this part can be used repeatedly, and hence cost can be kept low.

When a conventional susceptor is used for epitaxial growth or the like, a SiC film of the susceptor is sublimated, and the resulting matter adheres to the back surface of a SiC wafer. Therefore, a conventional problem resides in the fact that the back surface of the wafer must be ground after epitaxial growth or thermal treatment is performed, in order to remove the SiC film adhering thereto. However, according to the susceptor of the present invention, the part on which the wafer is placed and the area around this part are the coating films of TaC, and hence the SiC film and the TaC film do not adhere to the back surface of the SiC wafer. Therefore, advantageously, the step of grinding the back surface of the SiC wafer can be removed.

Preferably, in the susceptor of the present invention, a graphite base material forming the graphite material covered with SiC or the graphite material covered with TaC has gas emission of $10^{-4}$ Pa/g or less at a standard temperature of 1000° C., and has a nitrogen content of $5 \times 10^{18}$ atoms/cm³ or less that is measured according to the SIMS analysis method. The gas emission mentioned above denotes the emission of $N_2$, $H_2$, $H_2O$, $CO$, $CO_2$, and hydrocarbon gases, such as $C_2H_4$ or $C_3H_8$. In proportion to the emission of $N_2$, $H_2$, $H_2O$, $CO$, and $CO_2$ excluding the hydrocarbon gases thereamong, the denseness of the coating film will become low when the coating film is formed according to the heat CVD method. Additionally, if the graphite base material contains these gases in a high content ratio, the denseness of the TaC film or the SiC film will also deteriorate. Additionally, if the graphite base material contains a gas such as $N_2$ in a high content ratio, N (nitrogen) or O (oxygen) will be taken into the TaC film and the SiC film. As a result, gases contained in the graphite base material are discharged through the coating film reduced in denseness during epitaxial growth or thermal treatment, and the coating film is worn down, thereby discharging impurities contained therein. Accordingly, the impurities are taken into produced semiconductor crystals, and defective purity will be caused.

According to the structure mentioned above, the gas emission is lowered, and the graphite base material in which a nitrogen content has been reduced is used, and hence it is possible to provide a susceptor capable of preventing the occurrence of the defect in purity of semiconductor crystals.

Preferably, in the susceptor of the present invention, a graphite base material forming the graphite material covered with SiC or the graphite material covered with TaC has an ash content of 10 ppm or less, and has a boron content of $5 \times 10^{16}$ atoms/cm$^3$ or less that is measured according to a SIMS analysis method. In proportion to an increase in the amount of the ash contained in the graphite base material, the denseness of the coating film becomes low when the coating film is formed according to the heat CVD method. Additionally, if the graphite base material contains boron in a high content ratio, this boron will be taken into the TaC film and the SiC film. As a result, impurities are taken into produced semiconductor crystals during epitaxial growth or thermal treatment, and a defect in purity will be caused.

According to the structure mentioned above, the ash content in the graphite base material is small, and the graphite base material in which a boron content has been reduced is used. Therefore, it is possible to provide a susceptor capable of preventing the occurrence of the defect in purity of semiconductor crystals.

The susceptor of the present invention can be used for epitaxial growth, for thermal treatment, for manufacturing silicon carbide semiconductors, or for manufacturing nitride semiconductors.

BEST MODE FOR CARRYING OUT THE INVENTION

Embodiments of the present invention will be described with reference to the attached drawings. First, a susceptor according to a first embodiment of the present invention will be described. The upper part of FIG. 1 is a perspective view of the susceptor according to the first embodiment of the present invention, and the lower part of FIG. 1 is a cross-sectional view thereof.

The susceptor 1 according to the first embodiment is composed of a graphite-made susceptor body 2 covered with SiC and a member 3 that forms a counter-sunk portion 3a in cooperation with the susceptor body 2 and that has its upper part on which a wafer is placed.

The susceptor body 2 has a stepwise hole into which the member 3 is fitted at its center. Preferably, the thickness of the SiC film with which the surface of the susceptor body 2 is covered is 10 to 300 μm. The reason why its thickness is 10 μm or more is that 10 μm is a minimum required thickness to completely cover the surface of the graphite base material therewith. More preferably, the thickness of the SiC film is 30 μm or more. The reason why its thickness is below 300 μm is from the viewpoint of time consumed for a covering operation, manufacturing costs, or dimensional accuracy of a product.

The member 3 is a disk-like member made of TaC, and has substantially the same shape as the capital letter T in cross-section. When fitted into the susceptor body 2, the member 3 can form the counter-sunk portion 3a that has a shape extremely suitable to arrange a wafer in the susceptor 1. The counter-sunk portion 3a is not required to have a flat shape equal in size to the wafer placed thereon, and may have a flat shape slightly larger in size than the wafer. As shown in FIG. 2, the member 3 may be replaced with a member 4 that is a TaC-covered graphite material in which the surface of graphite 6 is covered with a coating film 5 of TaC. In this case, preferably, the thickness of the TaC film is 10 to 100 μm, and more preferably 30 to 100 μm.

Since the thus structured susceptor 1 has the graphite-made susceptor body 2 covered with SiC, Si concentration and C concentration around the wafer can be kept constant. Additionally, since a difference in thermal expansion does not arise during epitaxial growth even if a SiC layer is deposited on the susceptor body 2, the SiC layer is never peeled off, thus making it possible to prevent the generation of particles. Additionally, since the member 3 used as an element on which a wafer is placed can be detached, the member 3 can be easily exchanged for another, for example, even when the member 3 deteriorates after epitaxial growth or thermal treatment is performed a plurality of times. As a result, the susceptor body 2 can be used repeatedly, and hence cost can be kept low. In contrast, even when only the susceptor body 2 deteriorates, the susceptor body 2 can be easily exchanged for another, and the member 3 can be used repeatedly.

Next, a susceptor according to a second embodiment of the present invention will be described. FIG. 3 is a cross-sectional view of the susceptor according to the second embodiment of the present invention. In this embodiment, a description of the same element as in the susceptor 1 according to the first embodiment is appropriately omitted.

The susceptor 7 according to the second embodiment is composed of a graphite-made susceptor body 2 covered with SiC, a member 8 used as an element on which a wafer is placed, and a SiC-made annular member 9 provided so as to be joined to the member 8 along the outer periphery of the upper part of the member 8. A counter-sunk portion 8a is formed by the susceptor body 2, the member 8, and the annular member 9.

The member 8 is a disk-like member made of TaC, and has substantially the same shape as the capital letter T in cross-section. When fitted into the susceptor body 2 together with the annular member 9, the member 8 can form the counter-sunk portion 8a that has a shape extremely suitable to arrange a wafer in the susceptor 7. The counter-sunk portion 8a is not required to have a flat shape equal in size to the wafer placed thereon, and may have a flat shape slightly larger in size than the wafer. Like the member 3 mentioned above, as shown in FIG. 2, the member 8 may be replaced with a member 4 that is a TaC-covered graphite material in which the surface of graphite 6 is covered with a coating film 5 of TaC. In this case, preferably, the thickness of the TaC film is 10 to 100 μm, and more preferably 30 to 100 μm.

Since the thus structured susceptor 7 has the graphite-made susceptor body 2 covered with SiC and the SiC-made annular member 9, Si concentration and C concentration around the wafer can be kept constant. Additionally, since a difference in thermal expansion does not arise during epitaxial growth even if a SiC layer is deposited on the susceptor body 2 and the annular member 9, the SiC layer is never peeled off, thus making it possible to prevent the generation of particles. Additionally, since the member 8 used as an element on which a wafer is placed and the annular member 9 can be detached, these members 8 and 9 can be easily exchanged for another, for example, even when the members 8 and 9 deteriorate after epitaxial growth or thermal treatment is performed a plurality of times. As a result, the susceptor body 2 can be used repeatedly, and hence cost can be kept low. In contrast, even when only the susceptor body 2 deteriorates, the susceptor body 2 can be easily exchanged for another, and the member 8 and the annular member 9 can be used repeatedly.

EXAMPLES

Example 1

A susceptor used in this example has the same structure as that of the susceptor 1 according to the first embodiment shown in FIG. 1. The thickness of a SiC film of a susceptor body was set at 100 μm, and the thickness of the middle of a TaC member was set at 2 mm.

The thus structured susceptor of Example 1 was produced according to the following method. Isotropic graphite in which boron concentration is reduced below $2\times10^{16}$ atoms/cm$^3$ and in which nitrogen concentration is reduced below $1\times10^{17}$ atoms/cm$^3$ was used as a graphite base material of the susceptor body 2. This isotropic graphite was produced as follows. First, a carbon material used as a base of a high-purity carbon-based material according to the present invention is produced by use of an atmospheric graphitizing and highly-purifying furnace. Thereafter, a graphitized isotropic carbon material manufactured by Toyo Tanso Co., Ltd., is processed to have the shape of the susceptor body 2. The graphite base material molded into the shape of the susceptor body 2 is put into the graphitizing and highly-purifying furnace, is then heated to 2450° C. at 1 atm by gradually heating a heating element, and is supplied with halogen or a gas of its compound, such as dichlorodifluoromethane, (in which the supply flow rate is, for example, approximately 1 to 7 NLM, depending on the amount of the to-be-heated carbon material with which a container is filled) for approximately eight hours (highly-purifying step). Thereafter, the highly-purified carbon material obtained at the highly-purifying step is continuously held in the furnace having a temperature of 2250° C. under the reduced pressure, and is again supplied with halogen or a gas of its compound, such as dichlorodifluoromethane. The resulting material is processed for five hours without changing the reduced pressure of 1000 Pa in the container (ultrahighly-purifying step). Thereafter, the temperature is lowered to 1450° C. while the container pressure is kept at 10 Pa, and the material is held at 1450° C. for 48 hours ((nitrogen) gas removing step). After the nitrogen gas removing step is completed, the material is held at 100 Pa for one hour while introducing hydrogen into the furnace (hydrogenating process). Thereafter, an argon gas serving as a rare gas is introduced into the container, and the temperature is lowered to room temperature. After being lowered to the room temperature, the material is enclosed together with the argon gas in a bag made of a polyethylene film so as not to be exposed to the atmosphere, and is kept therein. This is used as the graphite base material of the susceptor body.

Thereafter, the graphite base material molded into the cross-sectional shape of the susceptor body 2 shown in FIG. 1 was put into a CVD furnace, and was sufficiently heated and degassed at 1450° C. under a reduced pressure. Thereafter, the furnace (whose volume is 300 liters) was filled with a hydrogen gas so as to reach a normal pressure, and the graphite base material was kept at 1300° C. The graphite base material was covered with SiC at 1300° C. while introducing a mixed gas composed of $CH_3SiCl_3$ serving as a source gas and $H_2$ serving as a carrier gas ($CH_3SiCl_3$ concentration: $CH_3SiCl_3/H_2=10.0$ vol %) at the flow rate of 15 SLM. What was produced in this way was used as the susceptor body of Example 1. The susceptor of Example 1 was produced by fitting a disk-like member made of TaC to this susceptor body.

Example 2

Except that the disk-like member covered with TaC shown in FIG. 2 was used, the susceptor of Example 2 has the same structure as the susceptor 1 according to the first embodiment shown in FIG. 1. The thickness of the SiC film of the susceptor body was set at 100 μm, and the thickness of the TaC film of the disk-like member was set at 50 μm. The thus structured susceptor of Example 2 was produced according to the following method. The SiC film of the susceptor body was formed by being applied onto the surface of the same graphite base material as in Example 1 according to the same method as in Example 1. An isotropic graphite material that had undergone the same highly-purifying process as the susceptor body of Example 1 was used as the graphite base material of the disk-like member. Thereafter, the graphite base material formed in the shape of the graphite 6 shown in FIG. 2 was put into a CVD furnace, and was sufficiently heated and degassed at 1450° C. under a reduced pressure. Thereafter, the temperature of the furnace (whose volume is 300 liters) was kept at 1200° C. The graphite base material was covered with TaC while introducing a mixed gas composed of $TaCl_5$ and $CH_4$ both of which serve as a source gas and $H_2$ serving as a carrier gas ($TaCl_5:CH_4:H_2=10.0$ vol %: 20.0 vol %: 70.0 vol %) at the flow rate of 15 SLM. What was produced in this way was used as the disk-like member of Example 2. The susceptor of Example 2 was produced by fitting this disk-like member to the susceptor body.

Comparative Example 1

As shown in FIG. 4, the susceptor 10 of Comparative Example 1 is composed of a counter-sunk portion 11 and graphite 13 whose whole surface is covered with a SiC film 12. The thickness of the SiC film 12 of the susceptor 10 of Comparative Example 1 is 100 μm.

The thus structured susceptor of Comparative Example 1 was formed and produced by applying a SiC film onto the surface of the same graphite base material as in Example 1 according to the same method as in the susceptor body of Example 1.

Comparative Example 2

The susceptor of Comparative Example 2 has the same shape as the susceptor of Comparative Example 1, and is composed of a counter-sunk portion and graphite whose whole surface is covered with a TaC film. The thickness of the TaC film of the susceptor of Comparative Example 2 is 50 μm.

The thus structured susceptor of Comparative Example 2 was formed and produced by applying a TaC film onto the surface of the same graphite base material as in Example 1 according to the same method as in the disk-like member of Example 2.

Thereafter, SiC epitaxial growth was performed in an atmosphere of 1600° C. while introducing $SiH_4$ (240 sccm) and $C_3H_8$ (180 sccm) both of which serve as a source gas and $H_2$ (1000 sccm) serving as a carrier gas by use of the susceptors of Examples 1 and 2 and Comparative Examples 1 and 2. The state of the susceptors and that of the wafers were then observed and measured. The SiC wafer used herein was 4H-SiC (0001) with an 8-degree off angle.

First, after SiC epitaxial growth was performed, it was confirmed whether adhesion between the susceptor and the wafer had occurred or not. In the susceptors of Examples 1 and 2 and Comparative Example 2 in which the TaC film or the TaC member was present on the back side of the wafer, adhesion therebetween did not occur. However, in the susceptor of Comparative Example 1, adhesion therebetween occurred.

Thereafter, in each susceptor of Examples 1 and 2 and Comparative Examples 1 and 2, the epitaxial growth mentioned above was performed five times. The wafer to be placed on the counter-sunk portion of the susceptor was replaced with another each time. The results obtained by measuring the boron concentration of the epitaxially-grown SiC layer are shown in Table 1 given below. A SIMS (Secondary Ion Mass Spectrometry) analysis method was employed to measure it. The SIMS analysis method can analyze a material composition by sputtering the surface of a material by use of ions (normally, $O_2^+$, $Cs^+$, and $Ga^+$) that have been accelerated to from several hundred V to 20 kV and then measuring the mass of positively- or negatively-charged particles that have been ejected therefrom. The greatest feature of the SIMS analysis method is that all elements ranging from $^1H$ to $^{238}U$ contained in the material can be detected.

TABLE 1

|  | Example 1 | Example 2 | Comparative Example 1 | Comparative Example 2 |
|---|---|---|---|---|
| First time | $2.4 \times 10^{14}$ | $3.1 \times 10^{14}$ | $2.4 \times 10^{14}$ | $4.4 \times 10^{14}$ |
| Second time | $7.3 \times 10^{13}$ | $3.4 \times 10^{14}$ | $3.2 \times 10^{14}$ | $2.8 \times 10^{14}$ |
| Third time | $2.2 \times 10^{14}$ | $8.8 \times 10^{13}$ | $4.3 \times 10^{14}$ | $1.3 \times 10^{14}$ |
| Fourth time | $3.4 \times 10^{14}$ | $3.8 \times 10^{14}$ | $2.5 \times 10^{15}$ | $9.3 \times 10^{13}$ |
| Fifth time | $3.2 \times 10^{14}$ | $3.6 \times 10^{14}$ | $1.2 \times 10^{16}$ | $4.0 \times 10^{14}$ |
|  |  |  |  | (atoms/cm³) |

From Table 1, it is understood that, when the susceptors of Examples 1 and 2 are used, the characteristics of the epitaxially-grown SiC layer are stable. In contrast, when the susceptor of Comparative Example 1 is used, the concentration of impurities becomes high by the fourth epitaxial growth. It was observed that the SiC film disposed right under the part on which the wafer was placed was evaporated, and the graphite base material was about to be bared. The susceptor of Comparative Example 2 covered with the TaC film did not cause such a problem.

Thereafter, in each susceptor of Examples 1 and 2 and Comparative Examples 1 and 2, epitaxial growth was performed five times, and it was observed whether the SiC layer was peeled off from the coating film of the susceptor. The results are shown in Table 2 given below. The wafer to be placed on the counter-sunk portion of the susceptor was replaced with another wafer each time. As shown in Table 2, in Comparative Example 2 using the susceptor including graphite covered with the TaC film, it was observed from the second epitaxial growth that the SiC layer deposited on the TaC film during epitaxial growth was peeled off therefrom. The peeling-off thereof causes the generation of particles, and causes a deterioration in characteristics of the epitaxially-grown SiC layer. In Examples 1 and 2 and Comparative Example 1, the peeling-off of the SiC layer was not observed.

TABLE 2

|  | Example 1 | Example 2 | Comparative Example 1 | Comparative Example 2 |
|---|---|---|---|---|
| First time | Not peeled off | Not peeled off | Not peeled off | Not peeled off |
| Second time | Not peeled off | Not peeled off | Not peeled off | Peeled off |
| Third time | Not peeled off | Not peeled off | Not peeled off | Peeled off |
| Fourth time | Not peeled off | Not peeled off | Not peeled off | Peeled off |
| Fifth time | Not peeled off | Not peeled off | Not peeled off | Peeled off |

Therefore, it is understood from Examples 1 and 2 that a susceptor capable of obtaining a high-quality SiC semiconductor crystal during epitaxial growth can be provided.

Examples 3 and 4, Comparative Examples 3 and 4

In Examples 3 and 4 and Comparative Examples 3 and 4, in order to facilitate the observation of matter that has adhered to the back surface of the SiC wafer, the following SiC wafer was used for each susceptor. In more detail, a two-side-ground wafer (4H-SiC (0001) with a 8-degree off angle) obtained by further smoothing the back surface of the same SiC wafer as in Examples 1 and 2 and Comparative Examples 1 and 2 was used for each susceptor of Examples 3 and 4 and Comparative Examples 3 and 4. The surface root-mean-square (RMS) roughness of the back surface of the wafer obtained before epitaxial growth is performed was 0.5 to 0.7 nm.

Thereafter, epitaxial growth was performed in an atmosphere of 1600° C. for ten hours while introducing $SiH_4$ (240 sccm) and $C_3H_8$ (180 sccm) both of which serve as a source gas and $H_2$ (1000 sccm) serving as a carrier gas by use of these susceptors of Examples 3 and 4 and Comparative Examples 3 and 4. The state of the susceptors and that of the wafers were then observed and measured.

First, after SiC epitaxial growth was performed, it was confirmed whether adhesion between the susceptor and the wafer occurred or not. FIG. 5A to FIG. 5C are photographs showing the surface condition of the back surface of the wafer observed through a Nomarski optical microscope. In detail, FIG. 5A is a photograph showing the surface condition of the back surface of the wafer before epitaxial growth is performed, FIG. 5B is a photograph showing the surface condition of the back surface of the wafer when the susceptor of Comparative Example 3 is used, and FIG. 5C is a photograph showing the surface condition of the back surface of the wafer when the susceptor of Example 3 is used. In comparison with the susceptor having a state of the back surface of the wafer exhibited before epitaxial growth is performed as shown in FIG. 5A, the susceptor of Comparative Example 3 with which the SiC film keeps in contact showed adhesion with the wafer and surface roughness of the back surface of the wafer as shown in FIG. 5B, and the SiC film was sublimated and caused to adhere thereto. However, in the susceptor of Example 3 in which the TaC film was in contact with the back surface of the wafer, adhesion with the wafer did not occur, and the TaC film was neither sublimated nor caused to adhere thereto as shown in FIG. 5C. Additionally, the back surface of the wafer was flat. Likewise, in Example 4 and Comparative Example 4, the same surface condition as in FIG. 5C was shown.

Thereafter, in each susceptor of Examples 3 and 4 and Comparative Examples 3 and 4, the epitaxial growth mentioned above was performed five times. The wafer to be placed on the counter-sunk portion of the susceptor was replaced with another each time. Table 3 shows the thickness of matter adhering to the back surface of the wafer during this epitaxial growth, the surface roughness of the back surface of the wafer, and the thickness of the TaC film and that of the SiC film disposed right under the part on which the wafer was placed. Concerning the thickness of the matter adhering to the back surface of the wafer, a cleavage cross-section of the wafer exhibited after epitaxial growth was performed was observed through a scanning electron microscope (SEM, manufactured by Hitachi, S-3200N). FIG. 6 shows a cross-sectional SEM photograph of the wafer treated in Comparative Example 3 after epitaxial growth was performed. Although both the wafer and the adhered matter are made of SiC, there is a difference therebetween in the concentration of impurities. Therefore, the contrast of the secondary electron image of the SEM is differently observed. The thickness of SiC adhering to the back surface of the wafer was 2 to 3 μm. On the other hand, adhered matter was not observed on the back surface of each wafer of Examples 3 and 4 and Comparative Example 4.

This was substantially the same as the surface roughness of the back surface of the wafer shown before epitaxial growth was performed.

Thereafter, the thickness of the TaC film and the thickness of the SiC film disposed right under the part on which the wafer was placed were measured. After epitaxial growth was performed five times, the susceptor was destroyed and analyzed so as to measure the thickness of the coating film. A scanning electron microscope (SEM, manufactured by Hitachi, S-3200N) was used to measure it. The SiC film and the TaC film disposed right under the part on which the wafer was placed were cleft, and their film thicknesses were measured while observing their cross-sections. From Table 3, it is understood that, in Comparative Example 3, the SiC film with 14 μm was worn down after epitaxial growth was performed five times. On the other hand, in Examples 3 and 4 and Comparative Example 4, it was not confirmed that the TaC film was worn down.

Thereafter, in each susceptor of Examples 3 and 4 and Comparative Examples 3 and 4, epitaxial growth was performed five times, and it was observed whether the SiC layer was peeled off from the coating film of the susceptor. The results are shown in Table 4 given below. The wafer to be placed on the counter-sunk portion of the susceptor was

TABLE 3

Thickness of matter adhering to the back surface of the wafer [μm] (Surface roughness of the back surface of the wafer [nm])

| | Example 3 | Example 4 | Comparative Example 3 | Comparative Example 4 |
|---|---|---|---|---|
| First time | 0 (0.7) | 0 (0.7) | 2.7 (105) | 0 (0.9) |
| Second time | 0 (0.7) | 0 (0.8) | 2.5 (110) | 0 (0.8) |
| Third time | 0 (0.9) | 0 (0.7) | 2.0 (103) | 0 (0.8) |
| Fourth time | 0 (0.7) | 0 (0.7) | 3.1 (121) | 0 (0.7) |
| Fifth time | 0 (0.8) | 0 (0.7) | 2.7 (120) | 0 (0.8) |
| Thickness of the worn film obtained after the fifth performance was completed (μm) | 0 | 0 | 14 | 0 |

Thereafter, the surface root-mean-square roughness RMS was measured with an atom force microscope (AFM, manufactured by Digital Instruments, Nanoscope IIIa). From Table 3, the surface roughness of the back surface of the wafer treated in Comparative Example 3 after epitaxial growth was performed is 103 to 121 nm, indicating that the surface is rough. Therefore, the back surface of the wafer was in a state necessitating a regrinding process. On the other hand, the surface roughness of the back surface of each wafer of Examples 3 and 4 and Comparative Example 4 is 0.7 to 0.9 nm, indicating that the surface is extremely flat.

replaced with another wafer each time. As shown in Table 4, in Comparative Example 4 using the susceptor including graphite covered with the TaC film, it was observed from the second epitaxial growth that the SiC layer deposited on the TaC film during epitaxial growth was peeled off therefrom. The peeling-off thereof causes the generation of particles, and causes a deterioration in characteristics of the epitaxially-grown SiC layer. In Examples 3 and 4 and Comparative Example 3, the peeling-off of the SiC layer was not observed.

TABLE 4

Whether the SiC layer was peeled off from the coating film of the susceptor
(Pit density of the epitaxially-grown SiC layer [pits/cm$^2$])

| | Example 3 | Example 4 | Comparative Example 3 | Comparative Example 4 |
|---|---|---|---|---|
| First time | Not peeled off (53) | Not peeled off (23) | Not peeled off (33) | Not peeled off (241) |
| Second time | Not peeled off (102) | Not peeled off (43) | Not peeled off (52) | Peeled off (962) |
| Third time | Not peeled off (84) | Not peeled off (12) | Not peeled off (121) | Peeled off (1221) |
| Fourth time | Not peeled off (52) | Not peeled off (52) | Not peeled off (133) | Peeled off (1155) |
| Fifth time | Not peeled off (125) | Not peeled off (82) | Not peeled off (126) | Peeled off (1360) |

Further, a state of an interface between the wafer and the surface of the epitaxially-grown SiC layer was observed in the reflective mode and the transparent mode of a Nomarski optical microscope. FIG. 7A is a photograph showing the interface between the wafer and the epitaxially-grown SiC layer of Comparative Example 4 observed in the transparent mode, and FIG. 7B is a photograph showing the surface of the SiC layer observed in the reflective mode. Black dots pointed by the arrow designate particles mixed thereinto. As shown in FIG. 7B, the surface on which the particles appeared had convex surface defects that are called "shallow pits" or "wavy pits". A pit density caused by the mixed particles was evaluated. As a result, the pit density was 12 to 133 pits/cm$^2$ in Example 3, Example 4, and Comparative Example 3. On the other hand, in Comparative Example 4, the pit density was 241 to 1360 pits/cm$^2$, which is greater by one rank in the numerical place than that shown in Examples 3 and 4 and Comparative Example 3. In Comparative Example 4, SiC flakes peeled off therefrom were scattered into the atmosphere, and were taken into the SiC layer, thus increasing defects.

Therefore, it is understood that, likewise, a susceptor capable of obtaining high-quality SiC semiconductor crystals when epitaxial growth is performed can be provided according to Examples 3 and 4.

Example 5

The susceptor in Example 5 has the shape of FIG. 1. First, a base material was produced to be a graphite material in which the nitrogen concentration was reduced to $1\times10^{17}$ atoms/cm$^3$ or less, and the boron concentration was reduced to $2\times10^{16}$ atoms/cm$^3$ or less with an ash content below 2 ppm at an outgassing rate of $10^{-4}$ Pa/g at a standard temperature of 1000° C. through the highly-purifying step, the ultrahighly-purifying step, the (nitrogen) gas removing step, and the hydrogenating step according to the same method as in Example 1. Thereafter, according to the heat CVD method, the surface of the graphite base material of the susceptor body 2 was covered with a SiC film of 100 μm. Further, according to the heat CVD method, the surface of the graphite base material of the member 3 was covered with a TaC film of 50 μm.

Comparative Example 5

The susceptor in Comparative Example 5 has the shape of FIG. 4. First, after the highly-purifying step was completed according to the same method as in Example 1, a base material was produced to be a graphite material by being cooled with a nitrogen gas and being kept in the atmosphere without performing the ultrahighly-purifying step, the (nitrogen) gas removing step, and the hydrogenating step. The graphite material was processed so that the nitrogen concentration becomes greater than $5\times10^{19}$ atoms/cm$^3$, and the boron concentration becomes greater than $1\times10^{19}$ atoms/cm$^3$ with an ash content of 300 ppm at an outgassing rate of $10^{-5}$ Pa/g at a standard temperature of 1000° C. Thereafter, according to the heat CVD method, the surface of the graphite base material 13 of the susceptor was covered with a SiC film of 100 μm.

Comparative Example 6

The susceptor in Comparative Example 6 has the shape of FIG. 4. First, after the highly-purifying step was completed according to the same method as in Example 1, a base material was produced to be a graphite material by being cooled with a nitrogen gas and being kept in the atmospheric without performing the ultrahighly-purifying step, the (nitrogen) gas removing step, and the hydrogenating step. The graphite material was processed so that the nitrogen concentration becomes greater than $5\times10^{19}$ atoms/cm$^3$, and the boron concentration becomes greater than $1\times10^{19}$ atoms/cm with an ash content of 300 ppm at an outgassing rate of $10^{-5}$ Pa/g at a standard temperature of 1000° C. Thereafter, according to the heat CVD method, the surface of the graphite base material 13 of the susceptor was covered with a TaC film of 50 μm.

Thereafter, in each susceptor of Example 5, Comparative Example 5, and Comparative Example 6, the epitaxial growth mentioned above was performed, and the gas transmission rate of the SiC film and the gas transmission rate of the TaC film of each susceptor were evaluated. The results are shown in Table 5 given below. The nitrogen gas transmission rate of the coating film is measured based on a description given in the document (Kamiyama Minehiro, Sogabe Toshiaki, Tanso (Carbon) No. 151 (1992) p. 8). FIG. 8 is a schematic view of a measuring apparatus.

In the following description, the term "primary side" designates a space closed with a primary-side pipe 25 (which has a tank, not shown, at a midway point), a cell 26, a stop valve 30, an exhaust valve 31, and a gate valve 32. The degree of vacuum of this space is referred to as a primary-side vacuum. The term "secondary side" designates a space closed with the cell 26, the gate valve 32, and an exhaust valve 33. The degree of vacuum of this space is referred to as a secondary-side vacuum.

TABLE 5

|  | Example 5 | Comparative Example 5 | Comparative Example 6 |
|---|---|---|---|
| Kind of the coating film | Silicon carbide/tantalum carbide | Silicon carbide | Tantalum carbide |
| Gas transmission rate of the silicon carbide film (cm$^2$/s) | $1.5 \times 10^{-9}$ | $4.5 \times 10^{-4}$ | — |
| Gas transmission rate of the tantalum carbide film (cm$^2$/s) | $8.7 \times 10^{-10}$ | — | $5.1 \times 10^{-4}$ |
| Nitrogen concentration of the epitaxially-grown SiC layer (atoms/cm$^3$) | $5.2 \times 10^{15}$ | $5.6 \times 10^{18}$ | $2.8 \times 10^{18}$ |
| Boron concentration of | $3.4 \times 10^{14}$ | $7.2 \times 10^{17}$ | $5.8 \times 10^{17}$ |

TABLE 5-continued

|  | Example 5 | Comparative Example 5 | Comparative Example 6 |
|---|---|---|---|
| the epitaxially-grown SiC layer (atoms/cm³) |  |  |  |

Next, a description will be given of the operation of the measuring apparatus shown in FIG. 8 and a method for measuring the gas transmission rate of the susceptor. A measurement sample used herein was obtained by machining a susceptor to have a disk-like shape with a diameter greater than 30 mm and sufficiently drying the resulting one before measurement. The measurement sample is set in the cell 26, the gate valve 32 and the exhaust valve 31 are then opened, and rough vacuuming is performed by a rotary vacuum pump 24. After vacuuming is performed to reach 100 Pa or less, the exhaust valve 31 is closed, and the exhaust valves 33 and 34 are opened. Thereafter, the cell 26, primary-side pipe 25 and the secondary-side tank 27 are depressurized by a rotary vacuum pump 29 and a turbo-molecular pump 28 so as to reach a fixed high vacuum value. Thereafter, it is confirmed by an ionization vacuum gauge 23 that the primary-side pipe 25 and the secondary-side tank 27 have reached a high vacuum state, and the exhaust valves 33 and 34 and the gate valve 32 are closed. Thereafter, the vacuum pump 29 and the turbo-molecular pump 28 are stopped. Thereafter, the stop valve 30 is opened, and $N_2$ gas is applied to the primary-side pipe 25 under fixed test pressure while being confirmed by a primary-side vacuum gauge 21. The $N_2$ gas flows from the primary side toward the secondary-side tank 27 through the measurement sample in the cell 26, so that the pressure of the secondary-side tank 27 starts rising. The rate of rise of the pressure is measured with a secondary-side pressure gauge 22. After the measuring apparatus is operated in this way, the gas transmission rate (K) of the measurement sample is calculated according to the following equations (1) and (2).

$$K=(QL)/(\Box PA) \qquad (1)$$

$$Q=(p_2-p_1)V_0 \mathbf{56}/t \qquad (2)$$

Herein, K is a nitrogen gas transmission rate, Q is the quantity of airflow, $\Box P$ is a difference in pressure between the primary-side tank and the secondary-side tank, A is a transmission area, L is the thickness of the measurement sample, $p_1$ is the initial pressure of the secondary-side tank, $p_2$ is the final pressure of the secondary-side tank, $V_0$ is the volume of the secondary-side tank, and t is a measuring time.

To calculate the nitrogen gas transmission rate ($K_2$) of the coating film, the nitrogen gas transmission rate ($K_0$) of the graphite material covered with the SiC film and the TaC film is first measured, and then the coating films are removed by being ground, and the nitrogen gas transmission rate ($K_1$) of only the graphite base material is measured. Thereafter, $K_2$ is calculated according to the following equation (3).

$$(L_1+L_2)/K_0=L_1/K_1+L_2/K_2 \qquad (3)$$

Herein, $L_1$ is the thickness of the graphite base material, and $L_2$ is the thickness of the coating film of SiC and TaC.

The gas transmission rate of the SiC film and the gas transmission rate of the TaC film of Example 5 obtained from the equations mentioned above were $1.5 \times 10^{-9}$ cm²/s and $8.7 \times 10^{-10}$ cm²/s, respectively, indicating that these coating films are dense. Accordingly, sufficient characteristics were shown to restrict the gas emission from the graphite base material. However, the gas transmission rates of the SiC film and the TaC film of Comparative Examples 5 and 6 obtained from the equations mentioned above were $4.5 \times 10^{-4}$ cm²/s and $5.1 \times 10^{-4}$ cm²/s, respectively, indicating that these gas transmission rates are large. Accordingly, gas contained in the graphite base material was allowed to pass through the coating films, and was emitted into the atmosphere. Additionally, in Comparative Examples 5 and 6, when the coating films were formed according to the heat CVD method, a large amount of gas was discharged from the graphite base material. Therefore, the film formation was obstructed, and the denseness of the coating films was deteriorated.

Further, the nitrogen concentration and the boron concentration of the epitaxially-grown SiC layer were measured. The results are shown in table 5. A SIMS analysis method was used to measure the concentrations. The nitrogen concentration and the boron concentration of the SiC layer obtained when the susceptor of Example 5 was used were $5.2 \times 10^{15}$ atoms/cm³ and $3.4 \times 10^{14}$ atoms/cm³, respectively. These were highly pure. However, the nitrogen concentration and the boron concentration of the SiC layer obtained when the susceptor of Comparative Example 5 was used were high, and high impurity concentration was shown resulting from the gas emission from the graphite base material. The nitrogen concentration and the boron concentration of the epitaxially-grown SiC layer obtained when the susceptors of Comparative Examples 5 and 6 were used were within the range of $5.8 \times 10^{17}$ atoms/cm³ to $5.6 \times 10^{18}$ atoms/cm³, indicating that these concentrations are high. High impurity concentration was shown resulting from the emission of gas passing through the TaC film from the graphite base material.

Therefore, according to Example 5, it is understood that a susceptor capable of obtaining high-quality SiC semiconductor crystals when epitaxial growth is performed can be provided.

The present invention can be carried out in variously modified forms within a range not departing from the technical concept mentioned in the appended claims, and is not limited to the embodiments and the examples described above.

BRIEF DESCRIPTION OF DRAWINGS

The upper drawing of FIG. 1 is a perspective view of a susceptor according to a first embodiment of the present invention, and the lower one is a cross-sectional view of the susceptor according to the first embodiment of the present invention.

FIG. 5A is a photograph showing the surface condition of the back surface of a wafer before epitaxial growth is performed, FIG. 5B is a photograph showing the surface condition of the back surface of a wafer when a susceptor of Comparative Example 3 is used, and FIG. 5C is a photograph showing the surface condition of the back surface of a wafer when a susceptor of Example 3 is used.

FIG. 7A and FIG. 7B are surface photographs, each showing a state of an interface between the wafer and the surface of the epitaxially-grown SiC layer when a susceptor of Comparative Example 4 observed through a Nomarski optical microscope is used. FIG. 7A is a photograph taken in a transparent mode, and FIG. 7B is a photograph taken in a reflective mode.

Figure 1:
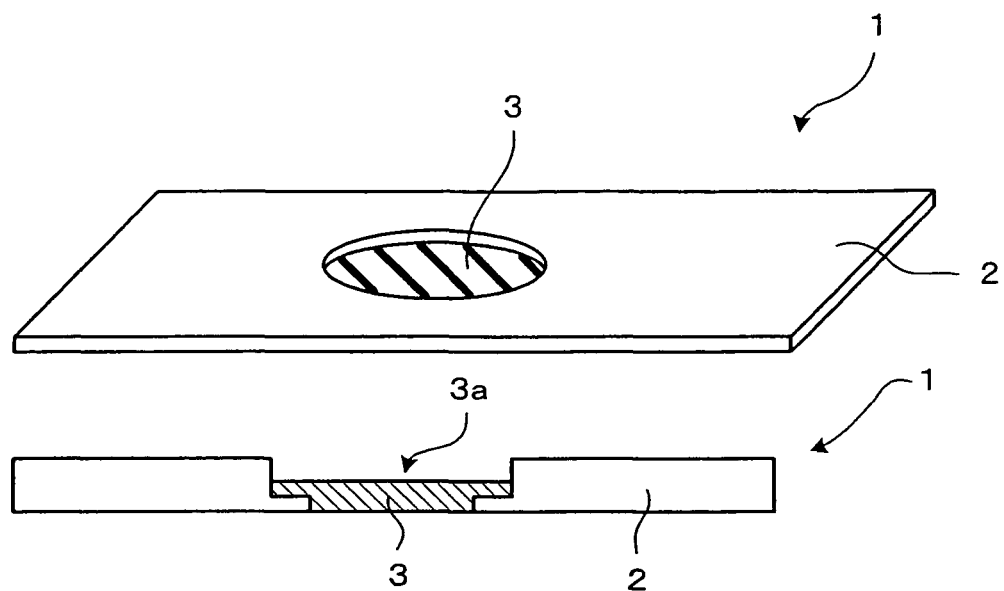
Figure 2:
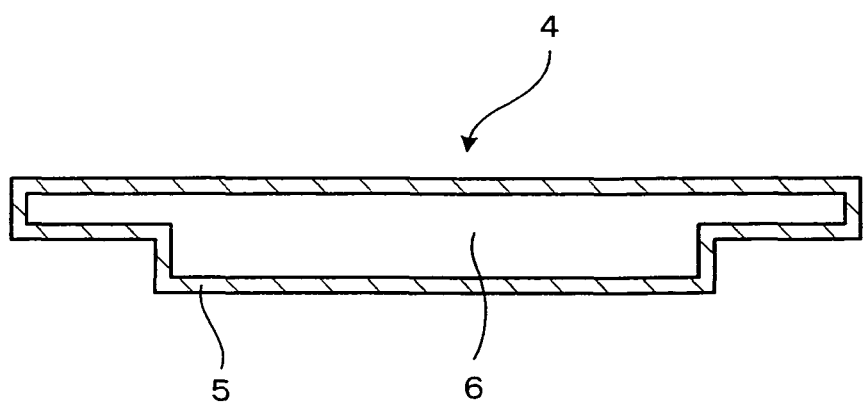
FIG. 2 is a conceptual cross-sectional view showing a modification of a disk-like member of the susceptor of FIG. 1.
Figure 3:
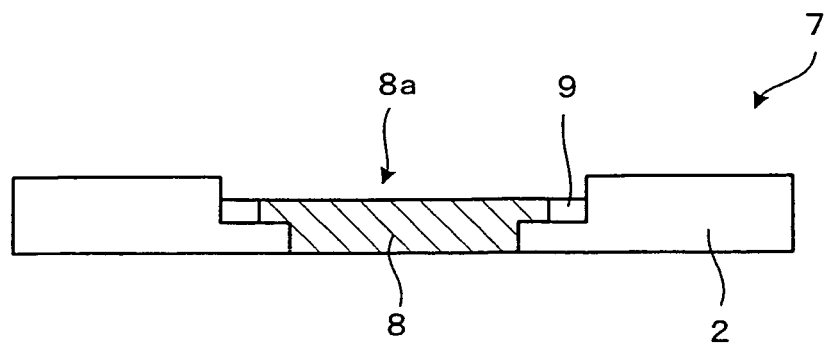
FIG. 3 is a cross-sectional view of a susceptor according to a second embodiment of the present invention.
Figure 4:
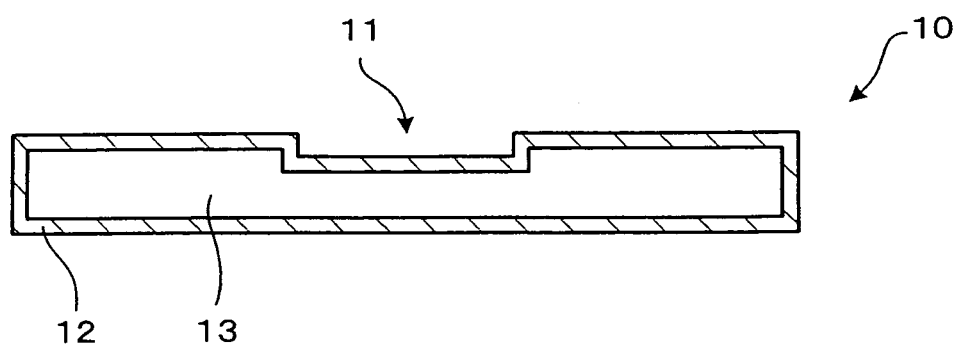
FIG. 4 is a conceptual cross-sectional view of a susceptor according to a comparative example.
Figure 5A:
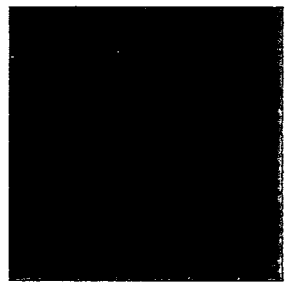
FIG. 5A to FIG. 5C are photographs showing the surface condition of the back surface of a wafer observed through a Nomarski optical microscope.
Figure 5B:
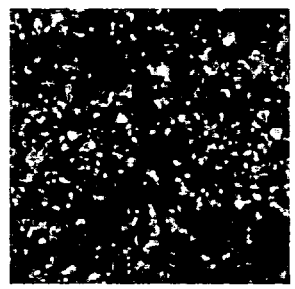
Figure 5C:
Figure 6:
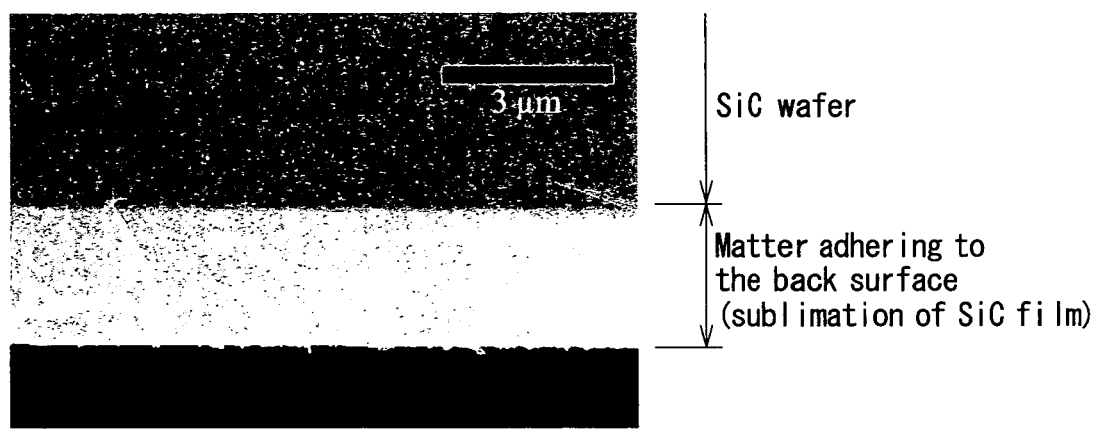
FIG. 6 is a cross-sectional SEM photograph near the back surface of the wafer when the susceptor of Comparative Example 3 is used.
Figure 8:
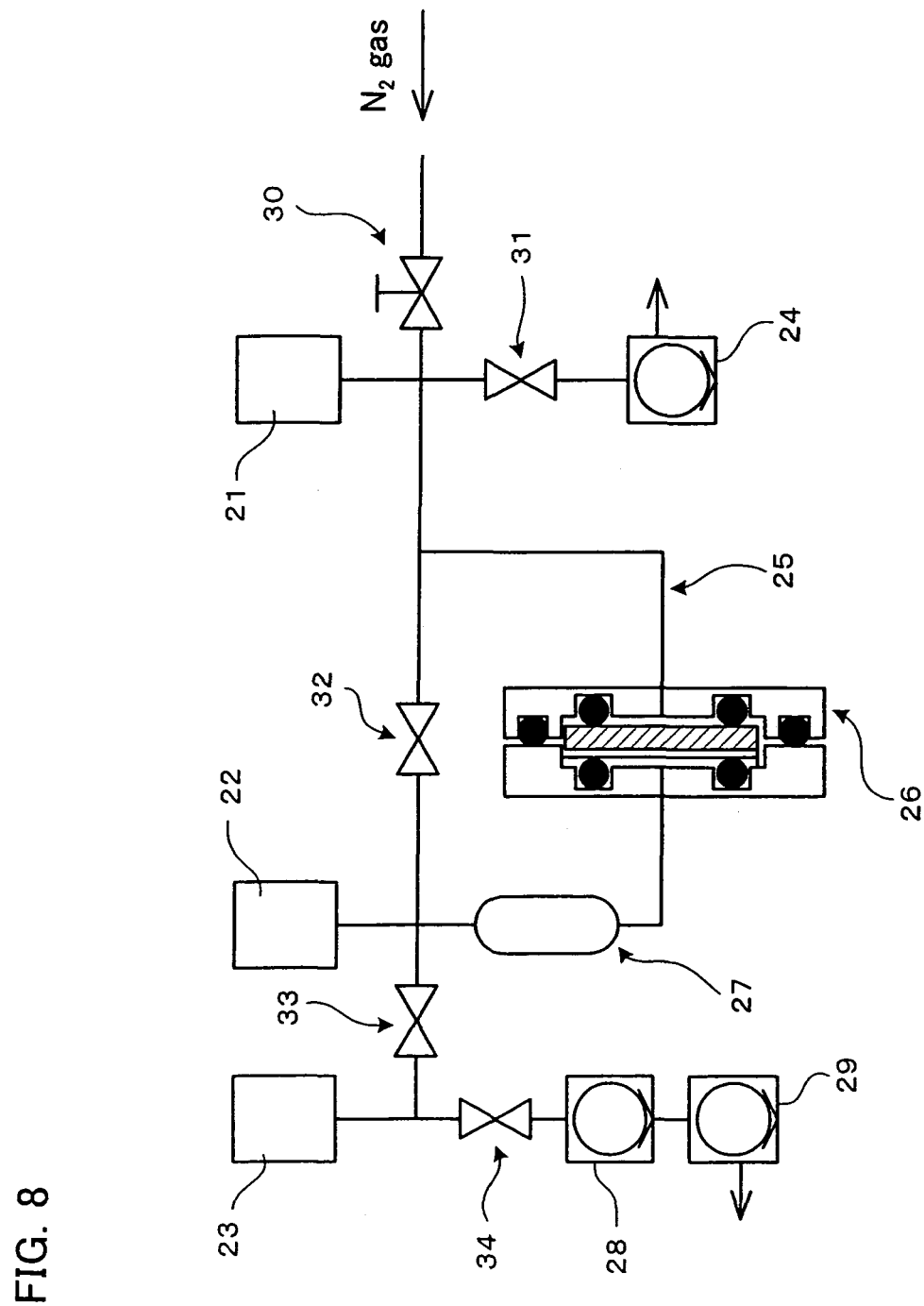
FIG. 8 is a schematic view of a gas-transmission-rate measuring apparatus.

DESCRIPTION OF REFERENCE CHARACTERS 1, 7, 10 Susceptor
2 Susceptor body
3, 4, 8 Member
3a, 8a, 11 Counter-sunk portion
5, 12 TaC film
6, 13 Graphite
9 Annular member
21 Primary-side vacuum gauge
22 Secondary-side vacuum gauge
23 Ionization vacuum gauge
24, 29 Rotary pump
25 Primary-side pipe
26 Transmission cell
27 Secondary-side tank
28 Turbo-molecular pump
30 Stop valve
31, 33, 34 Exhaust valve
32 Gate valve

The invention claimed is:

1. A susceptor, comprising:
a graphite-made body covered with silicon carbide; and
a wafer-placement part comprising tantalum carbide or a graphite material covered with a film of tantalum carbide,
wherein a through hole is formed on the graphite-made body,
the wafer-placement part is fitted into the through hole and contacts the graphite-made body,
a sunk portion is formed by the wafer-placement part and the graphite-made body covered with silicon carbide,
the wafer-placement part is exposed to an atmosphere at a bottom surface of the sunk portion,
the wafer-placement part comprises a substantially T-shaped cross section along a direction perpendicular to the bottom surface,
the through hole comprises a top opening and a bottom opening, wherein the top opening is larger than the bottom opening, and the body has a projection which projects inwardly from a wall defining the through hole, the projection supporting the wafer-placement part accommodated in the through hole,
the through hole comprises an upper hole which extends from an upper end of the through hole to an upper end of the projection and a lower hole which extends downward from the upper hole,
the projection forms a side surface defining the lower hole,
the lower hole is smaller in diameter than the upper hole,
the wafer-placement part comprises a larger-diameter portion which is larger than the bottom opening of the through hole and a small-diameter portion which is identical with or smaller in diameter than the bottom opening,
the large-diameter portion is housed in the upper hole and is placed on the projection when the wafer-placement part is housed in the through hole,
the small-diameter portion is housed in the lower hole,
a top surface of the wafer-placement part is a single plane, and
the susceptor is configured for a wafer to substantially cover the top surface of the wafer-placement part.

2. The susceptor of claim 1, wherein the wafer-placement part is detachable from the body.

3. The susceptor of claim 2, wherein a graphite base material forming the graphite material covered with silicon carbide or the graphite material covered with tantalum carbide having a thickness of from 10 to 100 μm has gas emission of $10^{-4}$ Pa/g or less at a standard temperature of 1000° C., and has a nitrogen content of $5 \times 10$ atoms/cm$^3$ or less that is measured according to a SIMS analysis method.

4. The susceptor of claim 2, wherein a graphite base material forming the graphite material covered with silicon carbide or the graphite material covered with tantalum carbide having a thickness of from 10 to 100 μm has an ash content of 10 ppm or less, and has a boron content of $5 \times 10^{16}$ atoms/cm$^3$ or less that is measured according to a SIMS analysis method.

5. The susceptor of claim 1, wherein the wafer-placement part is not exposed at a surface outside the sunk portion, which surface leads to the bottom surface via a side surface of the sunk portion.

6. The susceptor of claim 1, further comprising an annular member comprising silicon carbide, which is disposed along the outer circumference of the wafer-placement part and which forms the sunk portion with the body and the wafer-placement part.

7. The susceptor of claim 6, wherein the annular member is detachable from the body.

8. The susceptor of claim 1, wherein a graphite base material forming the graphite material covered with silicon carbide or the graphite material covered with tantalum carbide having a thickness of from 10 to 100 μm has gas emission of $10^{-4}$ Pa/g or less at a standard temperature of 1000° C., and has a nitrogen content of $5 \times 10^{18}$ atoms/cm$^3$ or less that is measured according to a SIMS analysis method.

9. The susceptor of claim 1, wherein a graphite base material forming the graphite material covered with silicon carbide or the graphite material covered with tantalum carbide having a thickness of from 10 to 100 μm has an ash content of 10 ppm or less, and has a boron content of $5 \times 10^{16}$ atoms/cm' or less that is measured according to a SIMS analysis method.

10. The susceptor of claim 1, wherein at least one section on which a wafer is placed consists of tantalum carbide.

11. The susceptor of claim 1, wherein at least one section on which a wafer is placed comprises a graphite material covered with a film of tantalum carbide having a thickness of from 10 to 100 μm.

12. The susceptor according to claim 1, wherein, when the wafer-placement part is housed in the through hole, a lower end of the small-diameter portion is provided at a lower end of the lower hole.

* * * * *